United States Patent
He et al.

(10) Patent No.: US 9,194,981 B2
(45) Date of Patent: Nov. 24, 2015

(54) MERCAPTOFUNCTIONAL HIGH MUBETA EO CHROMOPHORES AND HIGH TG, LOW OPTICAL LOSS, COVALENTLY BONDED, HIGH MUBETA EO CHROMOPHORE CONTAINING POLYMERS AND METHODS OF SYNTHESIZING EO MATERIALS

(71) Applicant: CORNING INCORPORATED, Corning, NY (US)

(72) Inventors: Mingqian He, Horseheads, NY (US); Jianguo Wang, Horseheads, NY (US)

(73) Assignee: CORNING INCORPORATED, Corning, NY (US)

( * ) Notice: Subject to any disclaimer, the term of this patent is extended or adjusted under 35 U.S.C. 154(b) by 9 days.

(21) Appl. No.: 14/277,258

(22) Filed: May 14, 2014

(65) Prior Publication Data
US 2014/0246631 A1 Sep. 4, 2014

Related U.S. Application Data

(62) Division of application No. 13/915,046, filed on Jun. 11, 2013, now Pat. No. 8,754,187, which is a division of application No. 12/756,442, filed on Apr. 8, 2010, now Pat. No. 8,481,672, which is a division of application No. 11/418,101, filed on May 3, 2006, now Pat. No. 7,723,462.

(51) Int. Cl.
C08G 73/10 (2006.01)
C08G 75/14 (2006.01)
(Continued)

(52) U.S. Cl.
CPC .............. *G02B 1/04* (2013.01); *C07D 207/416* (2013.01); *C07D 307/68* (2013.01); *G02F 1/0018* (2013.01); *G02F 1/3611* (2013.01); *G02F 1/3614* (2013.01); *G02F 1/3615* (2013.01)

(58) Field of Classification Search
CPC ......................................................... C08G 73/10
USPC ......... 528/321, 322, 374, 170, 310, 403, 423, 528/425; 252/583
See application file for complete search history.

(56) References Cited

U.S. PATENT DOCUMENTS

| 6,077,928 A | 6/2000 | Suh et al. .................... 528/170 |
| 6,393,190 B1 | 5/2002 | He et al. .................... 385/130 |

(Continued)

FOREIGN PATENT DOCUMENTS

| EP | 1772458 | 4/2007 |
| JP | 48-20900 | 3/1975 |

(Continued)

OTHER PUBLICATIONS

Machine Translation of JP1983016232.
(Continued)

*Primary Examiner* — Duc Truong

(57) ABSTRACT

The present invention relates generally to mercaptofunctional high μβ EO chromophores and EO polymers, and particularly to mercaptofunctional high μβ EO chromophores and EO polymers useful for making electro-optical devices and systems. Mercaptofunctional high μβ EO chromophores are covalently bonded to poly(imido sulfide) polymers producing high Tg, low optical loss, covalently bonded, high μβ EO chromophore containing polymers. Methods of synthesizing these EO materials using mild polymerization conditions are also described.

3 Claims, 1 Drawing Sheet

(51) Int. Cl.
*G02B 1/04* (2006.01)
*C07D 207/416* (2006.01)
*C07D 307/68* (2006.01)
*G02F 1/361* (2006.01)
*G02F 1/00* (2006.01)
*C08G 73/00* (2006.01)
*C08G 75/00* (2006.01)
*G02B 1/00* (2006.01)

(56) References Cited

U.S. PATENT DOCUMENTS

| | | | | |
|---|---|---|---|---|
| 6,503,421 | B1 | 1/2003 | Wang et al. | 252/582 |
| 6,514,434 | B1 | 2/2003 | He et al. | 252/582 |
| 6,584,266 | B1 | 6/2003 | He et al. | 385/130 |
| 7,723,462 | B2 | 5/2010 | He et al. | 528/374 |

FOREIGN PATENT DOCUMENTS

| | | |
|---|---|---|
| JP | 1983016232 | 1/1983 |
| JP | 10-218994 | 8/1998 |
| JP | 10-232502 | 9/1998 |
| JP | 11-311816 | 11/1999 |
| JP | 2000-53672 | 2/2000 |
| JP | 2004-501159 | 1/2004 |
| JP | 2004-506630 | 3/2004 |
| JP | 2004-508430 | 3/2004 |
| JP | 2005-112749 | 4/2005 |
| JP | 2006-506689 | 2/2006 |
| JP | 2007-297547 | 11/2007 |
| JP | 2008-511728 | 4/2008 |
| WO | 01-98287 | 12/2001 |
| WO | 01-98310 | 12/2001 |
| WO | 02-36647 | 5/2002 |

OTHER PUBLICATIONS

Machine Translation of JP2004-506630.
Machine Translation of JP2004-501159.
Machine Translation of JP11-311816.
Machine Translation of JP2000-53672.
Machine Translation of JP2008-511728.
Machine Translation of JP2006-506689.
Machine Translation of JP2004-508430.
Abstract of JP57-108158.
Machine Translation of JP10-218994.
Machine Translation of JP2007-297547.
Machine Translation of JP2005-112749.
Samyn et al; "High Glass Transition Chromophore Funtionalised Poly(Maleimide-Styrene)s for Second-Order Nonlinear Optical Applications," Polymer, 41, 2000, 6049-6054.
D. Landman, "Advances in the Chemistry and Applications of Bismaleidmides," Dev. Reinf. Plast, 1986, 39-81.
Ren, Albert S. et al; "Trifunctionalized High-Chromophore and Its 3D Polyurethane Network With Enhanced NLO Alignment Stability for Electro-Optic Device Applications," Polymer Preprints (American Chemical Society, Division of Polymer Chemistry) 1999, 40(1), 160-161.
Zhang, Xin et al; "Bismaleimides Having Electron-Donating Chromophore Moieties: A New Approach Toward Monitoring the Process of Curing Based on Their Fluorescence Behavior;" Macromolecular Rapid Communications; 2001; 22; 983-987.
Curliss, David B. et al; "Cure Reaction Pathways of Bismaleimide Polymers: A Solid-State 15N NMR Investigation;" Macromolecules; 1998; 31; 6776-6782.
Mao, Shane S. H. et al; "Incorporation of High-Isoxazolone Chromophores Into Polyurethane Networ—Progress Towards Device Quality Second-Order NLO Materials" Book of Abstracts, 214$^{th}$ ACS National Meeting, Las Vegas, NY, Sep. 7-11, 1997, PMSE-327; Publisher: American Chemical Society, Washington, D.C.

Hutaibet, Camelia et al, "New Functional Poly (Bismaleimide-Ether)s: Synthesis and Characterization," Polymer-Plastics Technology and Engineering, 2001, 40, 89-102.
White, Jerry E. et al, "Nucleophilic Addition of Thiols to N-phenylitaconimide," Sulfur Lett, 1986, 4, 157-9.
Jeng, Ru-Jong et al, "Organic/Inorganic NLO Materials Based on Reactive Polyimides and Bulky Alkoxysilane Dye Via Sol/Gel Process," Polymers for Advanced Technologies, 2003, 14(1), 66-75.
Crivello, J. V. et al, "Photosensitive Polymers Containing Diaryliodonium Salt Groups in the Main Chain," Journal of Polymer Science, Polymer Chemistry Ediiion, 1979, 17, 3845-58.
Crivello, J. V. "Polylvtidothioethers," Macrornol, Synth, 1977, 6, 6, 91-3.
Crivello, J. V. "Polyiiviedotitioethers" Polym, Prepr., Amer. Chem. Soc., Div. Polym Chem, 1972, 13, 924-9.
Crivello, James V. et al, "Polyimidothioether-Polysulfide Block Polymers," Journal of Polymer Science, Polymer Chemistry Edition, 1975, 13, 1919-42.
White, Jerry E. et al "Polymerization of N,N'-Bismaleimido-4,4'—Diphenylmethane With Arenedithiols. Synthesis of Some New Polyimidosulphides," Poymer, 1984, 25, 850-4.
Zhang, Cheng et al "Progress Toward Device-Quality Second-Order Nonlinear Optical Materials. 4. A Trilink High μB NLO Chromophore in Thermoset Polyurethane: A 'Guest-Host' Approach to Larger Electrooptic Coefficients" Macromolecules 92001, 34(2), 253-261 Sep. 2000.
Regnier, N. et al; "Solid-State $^{13}$C-NMR Study on Bismaleimide/Diamine Polymerization: Structure, Control of Particle Size, and Mechanical Properties" Journal of Applied Polymer Science 2000, 78, 2379-2388.
White, J.E. et al; "Step-Growth Polymers From Bismaleimides. Synthesis and Reactions of Some New Polymides," Polym. Prepr. (Am. Chem. Soc., Div. Polym. Chem.) 1985, 26, 132-33.
Kannappan, V. et al "Synthesis and Characterization of Certain Thermotropic Liquid Crystalline Random Copolyesters Containing Azobenzene Moiety in the Main Chain," Journal of Polymer Materials (2002), 19(1), 65-74.
Sun, Sam Shajing et al, "Synthesis and Characterization of Maleic Anhydride Derived Crosslinkable Polymers for Nonlinear Optical Applications," Proceedings of SPIE The International Society for Optical Engineering (2000), 4106(Linear, Nonlinear, and Power Limiting Organics), 177-185.
Kim, Min Ho et al "Synthesis and Characterization of Nonlinear Optical Polymers Having Quinoline-Based Chromophores," Bulletin of the Korean Chemical Society (2002), 23(7), 964-970.
Leng, Weinan et al "Synthesis and Characterization of Nonlinear Optical Side-Chain Polyimides Containing the Benzothtazole Chromophores," Macromolecules (2001), 34(14), 4774-4779.
Ashok Kumar, A. et al; "Synthesis and Characterization of Siliconized EPDXY-1, 3-BIS (MALEIMIDO) Benzene Intercrosslinked Matrix Materials," Polymer 2001, 43, 693-702.
Misra, A.C. et al; "Synthesis and Properties of Some New Fluorine-Containing Polyimides," Polymer 1992, 33, 1078-82.
White, J.E. et al; "Synthesis and Properties of Some New Polyimidosulfides With Highly Mobile Backbones," J. Polym. Sci., Polym. Chem. Ed. 1984, 22, 589-96.
Sava, M.; "Syntheses of Bismaleimides With Ester Units and Their Polymerization With Diamines," Journal of Applied Polymer Science 2002, 84, 750-757.
He, Mingqian et al; "Synthesis of Chromophores With Extremely High Electro-Optic Activity. 1. Thiophene Bridge Based Chromophores," Chemistry of Materials (2002), 14(11), 4662-4668.
He, Mingqian et al; "Synthesis of Chromophores With Extremely High Electro-Optic Activities. 2. Isophorone and Combined Isophorone Thiophene Based Chromophores," Chemistry of Materials (2002), 14(11), 4669-4675.
Lee, Ju-Yeon et al; "Synthesis of Polyurethanes Containing Dioxybenzylidenecyanoacetate As An NLO-Chromophore for Electro-Optic Applications," Journal of Macromolecular Science, Pure and Applied Chemistry (2001), A38(9), 973-980.
Gaina, V. et al "Thermal Characterization of Polyaminobismaleimide Prepolymers," Polymer-Plastics Technology and Engineering 2001, 40, 89-102.

(56) References Cited

OTHER PUBLICATIONS

Jeng, Ru-Jong et al "Thermally Stable NLO Materials Based on Organosoluble Polyimides and an Alkoxysilane Dye Via Sol-Gel Process," Journal of Macromolecular Science, Pure and Applied Chemistry (2001), A38(8), 821-837.

Ryu, Mi-Kyung et al; "Synthesis and Characterization of Silicon-Containing Side Chain NLO Polyesters" Polymeric Materials Science and Engineering (1996), 75 253-254.

White, J.E., "Synthesis and Properties of High-Molecular-Weight Step-Growth Polymers From Bismaleimides," Ind. Eng. Chem. Prod. Res. Dev. 1986, 25, 395-400.

Misra, A.C. et al "Synthesis and Properties of Octafluoro-Benzidine BIS-MALEIM1DE and of Its Reaction Products With Fluorinated Diamines," Polymer 1992, 33, 1083-9.

He et al., "Chromophores-Comprising the Same," 2002; Corning Incorporated; Chem. Abstract; 136: 387425.

He et al, "Chromophores-Optical Waveguides," 2001; Corning Incorporated; Chem. Abstract 136:55226.

MERCAPTOFUNCTIONAL HIGH MUBETA EO CHROMOPHORES AND HIGH TG, LOW OPTICAL LOSS, COVALENTLY BONDED, HIGH MUBETA EO CHROMOPHORE CONTAINING POLYMERS AND METHODS OF SYNTHESIZING EO MATERIALS

CROSS-REFERENCE TO RELATED APPLICATIONS

This application is a divisional application of and claims the benefit of priority to U.S. patent application Ser. No. 13/915,046, filed on Jun. 11, 2013 now U.S. Pat. No. 8,754,187, which is a divisional application of and claims the benefit of priority to U.S. patent application Ser. No. 12/756,442, filed on Apr. 8, 2010 now U.S. Pat. No. 8,481,672, which is a divisional application of and claims the benefit of priority to U.S. Pat. No. 7,723,462, filed on May 3, 2006, the contents of all of which are relied upon and incorporated herein by reference in their entirety.

BACKGROUND

1. Field of the Invention

The present invention relates generally to mercaptofunctional high dipole moment and hyperpolarizability ($\mu\beta$) electro-optic (EO) chromophores and EO polymers, and particularly to mercaptofunctional high $\mu\beta$ EO chromophores and EO polymers useful for making electro-optical devices and systems.

2. Technical Background

Organic chromophores are a basic element needed to build organic polymeric electro-optic materials. Traditionally, organic polymeric EO materials are made via the polymerization of EO chromophores which usually include dihydroxyl functional groups. EO materials are useful in systems and devices for emitting, modulating, transmitting or sensing light. EO chromophores bearing amino, vinyl and carboxylic acid functional groups have also been used in synthesizing organic polymeric EO materials. Organic polymeric EO materials such as polyesters, polyimides and polyurethanes have been synthesized from these monomers.

However, materials such as polyesters, polyimides and polyurethanes have several disadvantages. For example, in order to synthesize some of these polymers, a harsh reaction environment such as acidic or basic reaction conditions are needed; and in addition high temperatures are needed for the polymerization reaction to occur. These harsh polymerization conditions usually result in the destruction of the EO chromophores. Another disadvantage of EO chromophores bearing hydroxyl or amino functional groups is that these chromophores usually cause a large optical loss at major communication wavelengths, for example at 1550 nm.

Mercaptofunctional high $\mu\beta$ EO chromophores are especially sensitive to harsh polymerization conditions and are not stable to basic, acidic and free radical polymerization conditions. However, mercaptofunctional high $\mu\beta$ EO chromophores are advantageous for use in organic polymeric EO materials due to the low optical loss associated with —SH functional groups on the chromophore. The incorporation of these —SH chromophores into electro-optical polymers has proven challenging due to the sensitivity of the chromophores' terminal —SH groups. Several years have been spent trying to determine alternative polymerization reactions that can be carried out under mild polymerization conditions to produce organic polymeric EO materials having high glass transition (Tg) temperatures with low optical loss at communication wavelengths.

Organic polymeric EO materials having the following properties would be particularly useful. First, the active component, the EO chromophore, should be thermally and photochemically stable. Second, the EO chromophore should have a high molecular nonlinearity while being compatible with the polymer host material. Third, both the EO chromophore and the polymer host materials should possess optical transparency at communication wavelengths. Fourth, the EO chromophore should be able to be aligned in a noncentersymmentric fashion by poling and should remain stable for many years while retaining a high EO coefficient.

Bismaleimides are known as high temperature thermosetting resins having high Tg temperatures (some greater than 200° C.). These thermosetting resins cure via addition polymerization to produce high performance polymeric materials. Bismaleimides can be reacted with diamines or dithiols forming Michael type adducts, polyimides, or poly(imido sulfides) through a step-growth polymerization mechanism. Although some complicated side reactions may occur in the reaction between bismaleimide and diamine or dithiols which can lead to the production of insoluble crosslinked polymers, a polymerization solvent having an acidic hydrogen atom can effectively suppress the side reactions from the anionic mechanism to give rise to linear polymers. During the 1980's, the structure and properties of different hydrocarbon poly(imido sulfide) materials were extensively investigated by General Electric and The Dow Chemical Company. However, Michael addition polymerization producing an EO chromophore containing poly(imido sulfide) polymer useful for organic polymeric EO materials and devices has presented challenges due to the harsh polymerization conditions typically required for a covalent bond between the poly(imido sulfide) polymer and the EO chromophore.

Octafluorobenzidine bismaleimide and its Michael adducts with fluorine-containing diamines are used in the preparation of highly fluorinated poly(imido amides). However, poly(imido amides) cannot be used for organic polymeric EO materials and devices at communication wavelengths, because of the strong absorption of NH groups in the polymer chain. Halogen-containing bismaleimide derivatives reacted with a diol are typically used to prepare polyetherpolyimides material for the optical communication industry. There is a low glass transition (Tg) disadvantage associated with some halogenated polymers such as halogenated acrylate polymers, in particular, fluorinated polyimides. Another disadvantage is the solvent process capability of fluorinated polyimides.

For the foregoing reasons, the technical challenge for synthesis of a high Tg, low optical loss, covalently bonded and high $\mu\beta$ EO chromophores containing polymers lies not only in the synthesis of the polymeric host material, but also in the polymerization reaction incorporating the EO chromophore into the final material. Since polymerization conditions as discussed above can destroy the unique donor, acceptor and electron rich bridge electronic structures of the high $\mu\beta$ chromophores, especially mercaptofunctional high $\mu\beta$ chromophores whose incorporation in EO materials would be advantageous due to the low optical loss associated with the —SH functional group, improved methods for synthesizing these materials is highly desirable.

SUMMARY OF THE INVENTION

Maleimide copolymers with low optical loss, high Tg and excellent solvent process capability have been developed and are described in U.S. Pat. No. 6,503,421 B1, the disclosure of which is incorporated herein by reference in its entirety, having a common assignee as the present invention. The maleimide copolymers described therein have been further developed in the present invention to produce novel poly(imido sulfide) polymeric and halogenated poly(imido sulfide) polymeric host materials for covalently bonding mercaptofunctional high μβ chromophores useful for organic polymeric EO materials and devices.

One embodiment of the present invention relates to electro-optical chromophores having general Formula I:

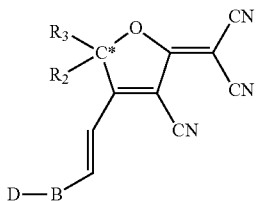

I wherein:

C* denotes a chiral carbon atom;

D is an electron donating group;

B comprises at least one bivalent ring;

$R_2$ and $R_3$ are different from one another; and $R_2$ is selected from the group consisting of H, substituted or unsubstituted $C_1$-$C_{10}$ alkyl, substituted or unsubstituted $C_2$-$C_{10}$ alkenyl, substituted or unsubstituted $C_2$-$C_{10}$ alkynyl, substituted or unsubstituted aryl, substituted or unsubstituted alkylaryl, substituted or unsubstituted carbocycle, substituted or unsubstituted heterocycle, substituted or unsubstituted cyclohexyl, and $(CH_2)_n$—O—$CH_2)_n$ where n is an integer from 1 through 10; and $R_3$ is selected from the group consisting of substituted or unsubstituted aryl, substituted or unsubstituted alkylaryl, substituted or unsubstituted carbocycle, substituted or unsubstituted heterocycle, substituted or unsubstituted cyclohexyl, and $(CH_2)_n$—O—$(CH_2)_n$ where n is an integer from 1 through 10;

or $R_2$ and $R_3$ together form a ring structure or a substituted ring structure; and the compound of Formula I has at any location, at least one terminal —SH group capable of reacting with a maleimide bond.

Another embodiment of the present invention relates to electro-optical polymers comprising at least one N-(halogenated phenyl) maleimide and at least one sulfide selected from the group consisting of substituted dithiols, di or bis(alkyl mercapto) sulfides, and halogenated di(mercapto) compounds.

Another embodiment of the present invention relates to electro-optic materials comprising a polymer having a poly(imido sulfide) backbone and an electro-optical chromophore having at least one terminal —SH group capable of reacting with a maleimide double bond, the —SH group being at any location on the EO chromophore.

Another embodiment of the present invention relates to a method of synthesizing an electro-optical material comprising a polymer having a poly(imido sulfide) backbone and an electro-optical chromophore having general Formula I:

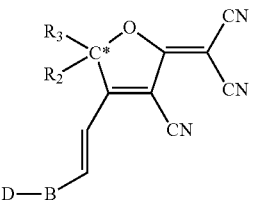

I the method comprising reacting a selected sulfide compound with a N-(halogenated biphenyl) bismaleimide and with the optical chromophore in a solvent utilizing a catalyst;

maintaining the reaction temperature between about 20° C. and about 60° C. for about two hours;

precipitating the resulting polymer into a solution of methanol and hydrochloric acid;

washing the resulting precipitated polymer with methanol;

drying the polymer in a vacuum oven at about 60° C. to about 80° C. for about 16 hours thereby obtaining an EO material;

wherein, in the compound of Formula I;

wherein:

C* denotes a chiral carbon atom;

D is an electron donating group;

B comprises at least one bivalent ring;

$R_2$ and $R_3$ are different from one another; and $R_2$ is selected from the group consisting of H, substituted or unsubstituted $C_1$-$C_{10}$ alkyl, substituted or unsubstituted $C_2$-$C_{10}$ alkenyl, substituted or unsubstituted $C_2$-$C_{10}$ alkynyl, substituted or unsubstituted aryl, substituted or unsubstituted alkylaryl, substituted or unsubstituted carbocycle, substituted or unsubstituted heterocycle, substituted or unsubstituted cyclohexyl, and $(CH_2)_n$—O—$CH_2)_n$ where n is an integer from 1 through 10; and $R_3$ is selected from the group consisting of substituted or unsubstituted aryl, substituted or unsubstituted alkylaryl, substituted or unsubstituted carbocycle, substituted or unsubstituted heterocycle, substituted or unsubstituted cyclohexyl, and $(CH_2)_n$—O—$(CH_2)_n$ where n is an integer from 1 through 10;

or $R_2$ and $R_3$ together form a ring structure or a substituted ring structure; and the compound of Formula I has at any location, at least one terminal —SH group capable of reacting with a maleimide bond forming a covalent bond.

Examples, without limitation, of the useful compounds include substituted dithiols, di or bis(alkyl mercapto) sulfides, and halogenated di(mercapto) compounds. [Note: generally, for drying all polymers described in this specification, the drying temperature is in the range of 60° C. to 80° C. and the drying time is until dry, typically in the range of 12 to 20 hours].

Another embodiment of the present invention relates to a method of synthesizing an electro-optical polymer comprising a N-(halogenated biphenyl) bismaleimide and at least one sulfide selected from the group consisting of substituted dithiols, di or bis(alkyl mercapto) sulfides, and halogenated di(mercapto) compounds, the method comprising:

reacting a sulfide with a N-(halogenated biphenyl) bismaleimide in a solvent utilizing a triamine catalyst for example, triethylamine;

maintaining the reaction temperature between about 20° C. and about 60° C. for about two hours;

precipitating the resulting polymer into a solution of methanol and hydrochloric acid;

washing the resulting precipitated polymer with methanol; and drying the polymer in a vacuum oven in the range of about 60° C. to about 80° C. for about 16 hours thereby obtaining an EO material.

Additional features and advantages of the invention will be set forth in the detailed description which follows, and in part will be readily apparent to those skilled in the art from the description or recognized by practicing the invention as described in the written description and claims hereof, as well as the appended drawings.

It is to be understood that both the foregoing general description and the following detailed description are merely exemplary of the invention, and are intended to provide an overview or framework to understanding the nature and character of the invention as it is claimed.

The accompanying drawings are included to provide a further understanding of the invention, and are incorporated in and constitute a part of this specification. The drawings illustrate one or more embodiment(s) of the invention and together with the description serve to explain the principles and operation of the invention.

BRIEF DESCRIPTION OF THE DRAWINGS

The invention is best understood from the following detailed description when read with the accompanying drawing figures.

DETAILED DESCRIPTION

Figure 1:
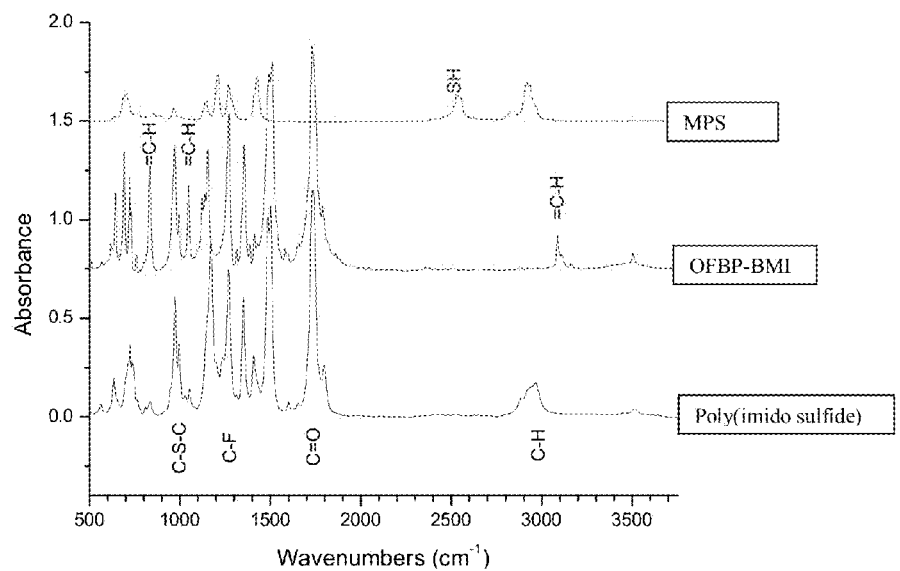
FIG. 1 is an EO polymer structure of the present invention as shown by FTIR results.

As used herein, the term "C*" designates a "chiral" carbon atom where the mirror image of the compound is different then the compound. In addition, "C*" can denote a spiro center when C* in combination with $R_2$ and $R_3$ forms a ring or substituted ring. In such instances, C* can be spiro and chiral or simply spiro.

The mercaptofunctional high μβ chromophores and organic polymeric electro-optic (EO) materials of the present invention improve the low Tg problem associated with fluorinated acrylate polymers and help to facilitate solvent process capability of halogenated polyimides, in particular fluorinated polyimides. Maleimide copolymers, in particular halogenated maleimide copolymers of the present invention, possess low optical loss, high Tg temperatures and excellent solvent process capability and higher thermal stability.

The present invention provides mercaptofunctional high μβ chromophores, poly(imido sulfide) and halogenated poly(imido sulfide) linear optic polymers and nonlinear optic polymeric materials incorporating EO chromophores. The present invention further provides methods of making the poly(imido sulfide) and halogenated poly(imido sulfide) linear optic polymers and nonlinear optic polymeric EO materials that allow mercaptofunctional chromophores to be copolymerized into a high Tg and low optical loss halogenated covalently bonded polymer matrix using very mild polymerization conditions. These methods, as further described below, minimize damage to the chromophore that is normally caused by using radical, acid or base catalysis with the sensitive mercaptofunctional high μβ chromophores during the polymerization reaction.

One embodiment of the present invention relates to electro-optical chromophores having general Formula I:

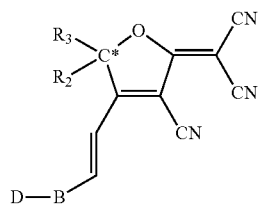

I wherein:
C* denotes a chiral carbon atom;
D is an electron donating group;
B comprises at least one bivalent ring;
$R_2$ and $R_3$ are different from one another; and
$R_2$ is selected from the group consisting of H, substituted or unsubstituted $C_1$-$C_{10}$ alkyl, substituted or unsubstituted $C_2$-$C_{10}$ alkenyl, substituted or unsubstituted $C_2$-$C_{10}$ alkynyl, substituted or unsubstituted aryl, substituted or unsubstituted alkylaryl, substituted or unsubstituted carbocycle, substituted or unsubstituted heterocycle, substituted or unsubstituted cyclohexyl, and $(CH_2)_n$—O—$CH_2)_n$ where n is an integer from 1 through 10; and
$R_3$ is selected from the group consisting of substituted or unsubstituted aryl, substituted or unsubstituted alkylaryl, substituted or unsubstituted carbocycle, substituted or unsubstituted heterocycle, substituted or unsubstituted cyclohexyl, and $(CH_2)_n$—O—$(CH_2)_n$ where n is an integer from 1 through 10;
or $R_2$ and $R_3$ together form a ring structure or a substituted ring structure; and
the compound of Formula I has, at any location, at least one terminal —SH group capable of reacting with a maleimide bond.

D is an electron donating group. Preferred electron donating groups are described in, for example, U.S. Pat. No. 6,584,266 B2, the disclosure of which is incorporated herein by reference in its entirety, having a common assignee as the present invention.

B is a cyclic bridge which couples the electron withdrawing group and the electron donating group. Preferably, B is at least one bivalent ring. Bivalent rings which can be employed as cyclic bridges in the present invention are also described in, for example, U.S. Pat. No. 6,584,266 B2.

Another embodiment of the present invention relates to electro-optical chromophores having Formula II:

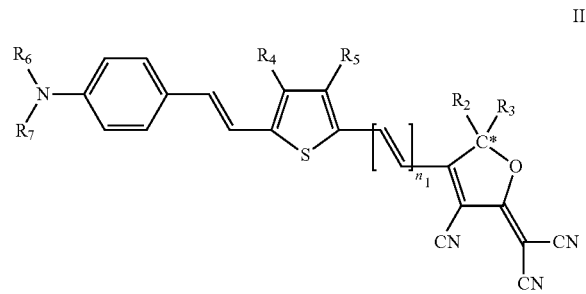

II wherein:
C* denotes a chiral carbon atom;
$R_2$ and $R_3$ are different from one another; and
$R_2$ is selected from the group consisting of H, substituted or unsubstituted $C_1$-$C_{10}$ alkyl, substituted or unsubstituted $C_2$-$C_{10}$ alkenyl, substituted or unsubstituted $C_2$-$C_{10}$ alkynyl, substituted or unsubstituted aryl, substituted or unsubstituted alkylaryl, substituted or unsubstituted carbocycle, substituted or unsubstituted heterocycle, substituted or unsubstituted cyclohexyl, and $(CH_2)_n$—O—$CH_2)_n$ where n is an integer from 1 through 10; and
$R_3$ is selected from the group consisting of substituted or unsubstituted aryl, substituted or unsubstituted alkylaryl, substituted or unsubstituted carbocycle, substituted or unsubstituted heterocycle, substituted or unsubstituted cyclohexyl, and $(CH_2)_n$—O—$(CH_2)_n$ where n is an integer from 1 through 10; or
$R_2$ and $R_3$ together form a ring structure or a substituted ring structure;
$R_4$ and $R_5$ can be the same or can be different and are selected from the group consisting of H, $C_nH_{2n+1}$, and SH; or
$R_4$ and $R_5$ together or separately form an aromatic compound;
$R_6$ and $R_7$ can be the same or can be different and are selected from the group consisting of H, $CH_3$, SH and $(CH)_{n2}$-Q, wherein Q is selected from the group consisting of H and SH and $n_2$ is an integer from 1 through 10; or
$R_6$ and $R_7$ together or separately form an aromatic compound;
$n_1$ is an integer from 1 through 3; and the compound of Formula II has, at any location, at least one terminal —SH group capable of reacting with a maleimide bond.

Exemplary electro-optic chromophores having Formula II are as follows, but are not limited to:

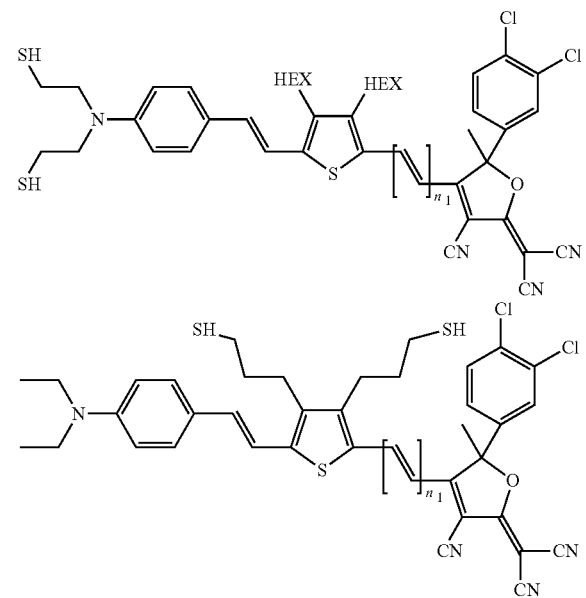

Electro-optic chromophores having Formula II can be synthesized by the following exemplary scheme:

Scheme 1

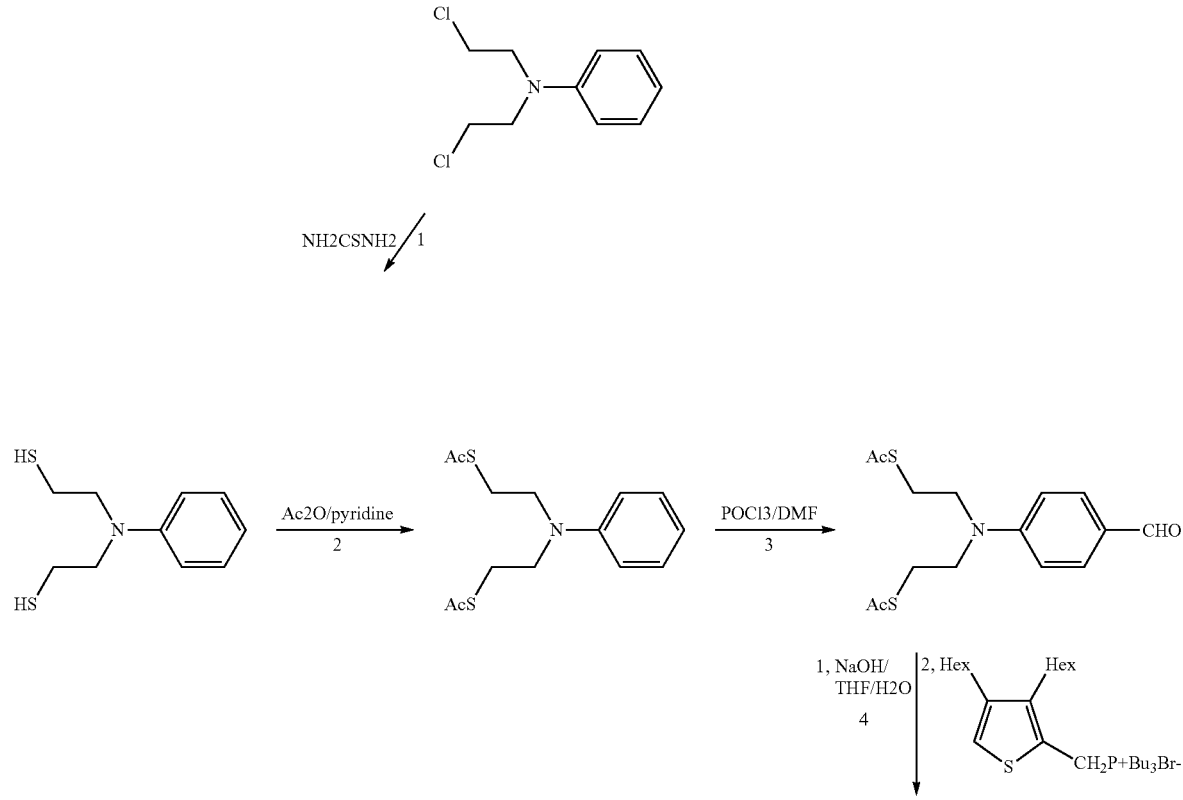

-continued

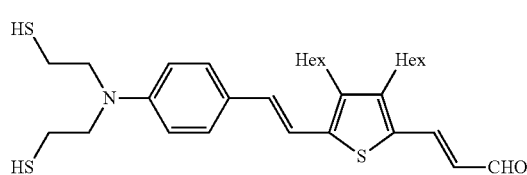
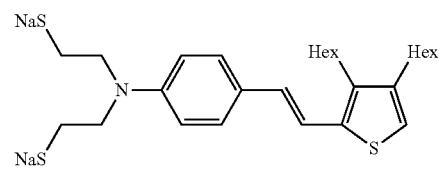

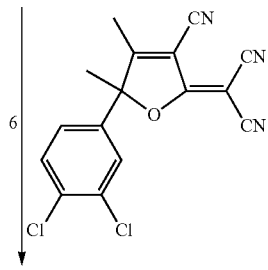

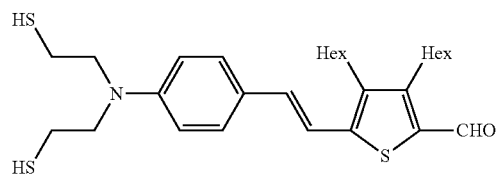

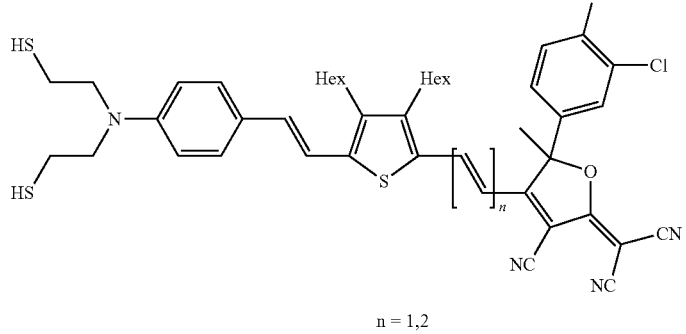

n = 1,2

Another embodiment of the present invention relates to electro-optical chromophores having Formula III:

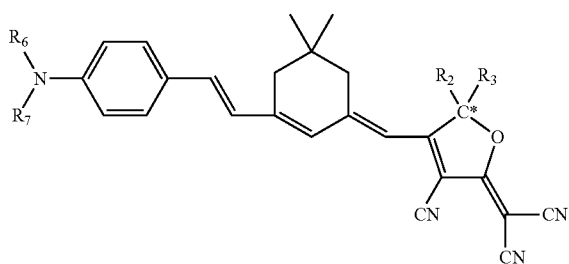

III wherein:
C* denotes a chiral carbon atom;
R$_2$ and R$_3$ are different from one another; and
R$_2$ is selected from the group consisting of H, substituted or unsubstituted C$_1$-C$_{10}$ alkyl, substituted or unsubstituted C$_2$-C$_{10}$ alkenyl, substituted or unsubstituted C$_2$-C$_{10}$ alkynyl, substituted or unsubstituted aryl, substituted or unsubstituted alkylaryl, substituted or unsubstituted carbocycle, substituted or unsubstituted heterocycle, substituted or unsubstituted cyclohexyl, and (CH$_2$)$_n$—O—CH$_2$)$_n$ where n is an integer from 1 through 10; and R$_3$ is selected from the group consisting of substituted or unsubstituted aryl, substituted or unsubstituted alkylaryl, substituted or unsubstituted carbocycle, substituted or unsubstituted heterocycle, substituted or unsubstituted cyclohexyl, and (CH$_2$)$_n$—O—(CH$_2$)$_n$ where n is an integer from 1 through 10; or R$_2$ and R$_3$ together form a ring structure or a substituted ring structure;

R$_6$ and R$_7$ can be the same or can be different and are selected from the group consisting of H, CH$_3$, SH and (CH)$_{n2}$-Q, wherein Q is selected from the group consisting of H and SH and n$_2$ is an integer from 1 through 10; or R$_6$ and R$_7$ together or separately form an aromatic compound; and the compound of Formula III has, at any location, at least one terminal —SH group capable of reacting with a maleimide bond.

Exemplary electro-optical chromophores having Formula III are as follows, but are not limited to:

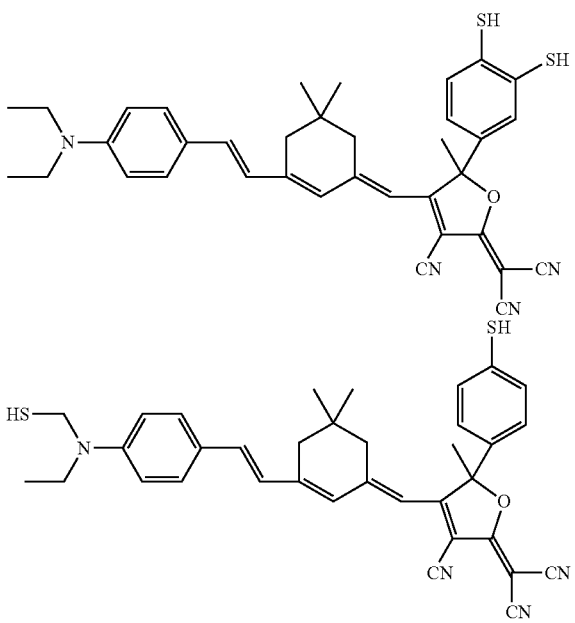

Another embodiment of the present invention relates to electro-optical polymers comprising at least one N-(halogenated phenyl) maleimide and at least one sulfide selected from the group consisting of substituted dithiols, di or bis (alkyl mercapto) sulfides, and halogenated di(mercapto) compounds.

Another embodiment of the present invention relates to electro-optical polymers comprising a N-(halogenated biphenyl) bismaleimide and at least one sulfide selected from the group consisting of substituted dithiols, di or bis(alkyl mercapto) sulfides, and halogenated di(mercapto) compounds.

The above-mentioned electro-optical polymers form novel poly(imido sulfides) of the present invention. Particularly useful poly(imido sulfides) have at least one N-(halogenated phenyl) maleimide having Formula IV:

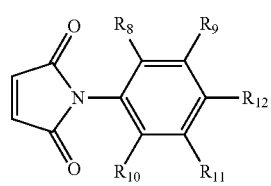

IV wherein:

$R_8$, $R_9$, $R_{10}$, $R_{11}$ and $R_{12}$ can be the same or can be different and are selected from the group consisting of H, F, Cl, Br, $CF_3$, $C_2$-$C_8$ fluoroalkyl and fluoroaryl; and at least one of $R_8$, $R_9$, $R_{10}$, $R_{11}$ and $R_{12}$ contains a halogen or a halogenated alkyl or aryl group.

Exemplary N-(halogenated phenyl) maleimides having Formula IV are described in U.S. Pat. No. 6,503,421 B1, the disclosure of which is incorporated herein by reference in its entirety, having a common assignee as the present invention. As described therein, perfluoro groups are especially useful. Examples of useful $R_8$, $R_9$, $R_{10}$, $R_{11}$ and $R_{12}$ groups include but are not limited to include $CF_3$, $C_2F_5$, $C_3F_7$, etc, perfluoroalkyl groups and $C_6F_5$ perfluoroaryl groups. Preferably, at least one of $R_8$, $R_9$, $R_{10}$, $R_{11}$ and $R_{12}$ contains fluorine. More preferably, at least one of $R_8$, $R_9$, $R_{10}$, $R_{11}$ and $R_{12}$ is fluorine, i.e., one, two, three or four of the $R_8$, $R_9$, $R_{10}$, $R_{11}$ and $R_{12}$ moieties are fluorine.

Exemplary poly(imido sulfides) are as follows, but are not limited to:

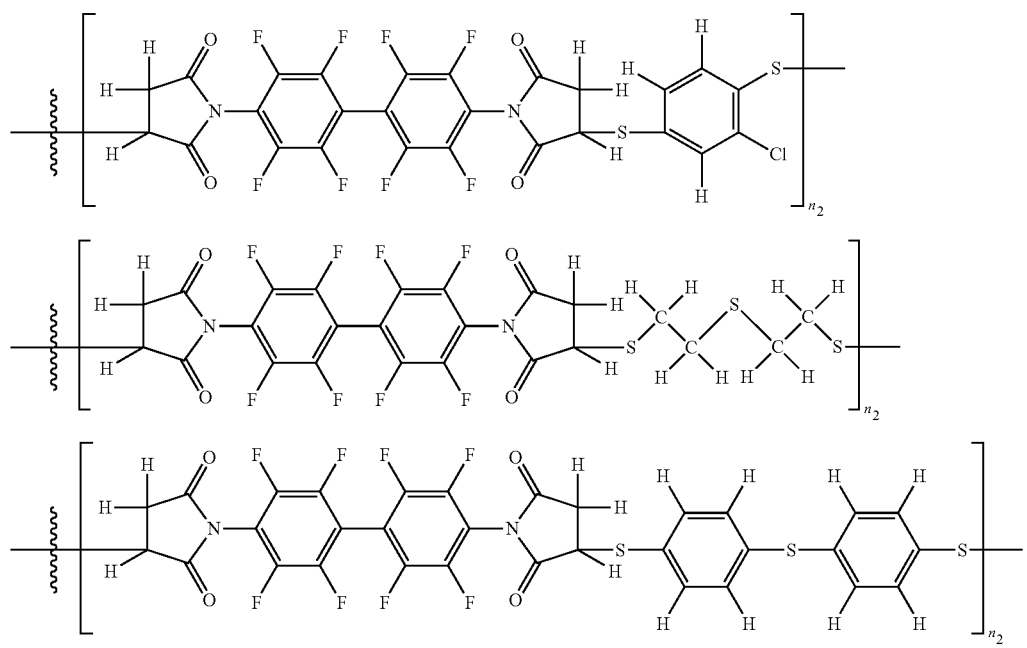

-continued

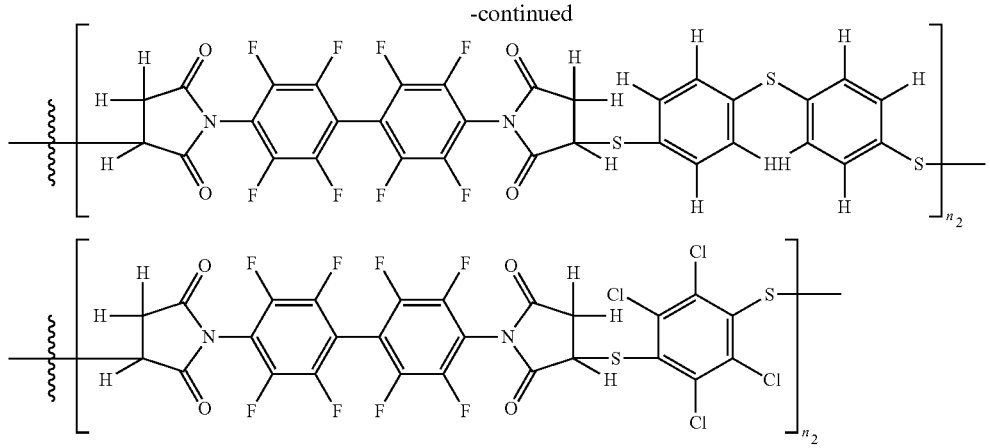

wherein:
$n_2$ is an integer greater than 20. Preferably, $n_2$ is an integer greater than 50.

Exemplary poly(imido sulfides) can be synthesized by the following exemplary scheme:

Scheme 2

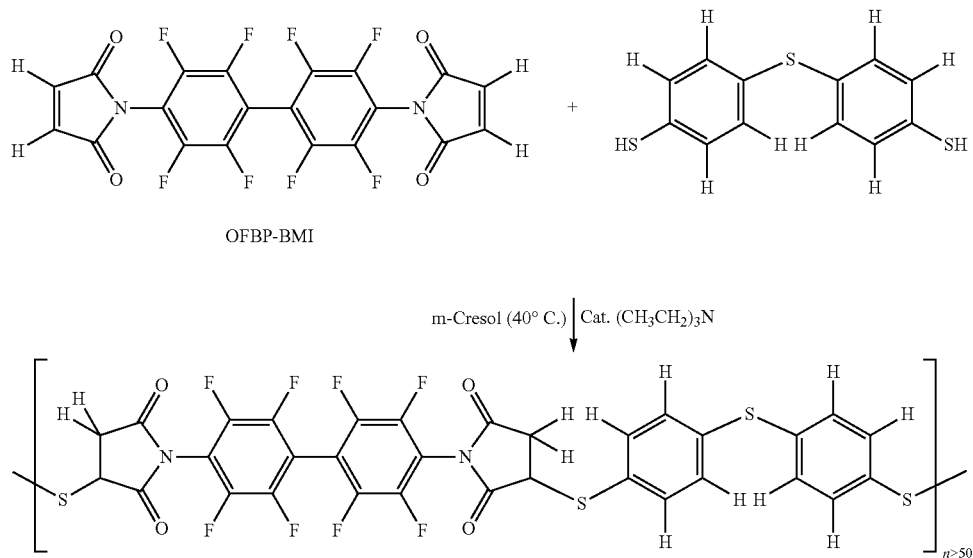

The octfluorobiphenyl bismaleimide (OFBP-BMI) monomer, 1,1'-(2,2',3,3',5,5',6,6'-octafluoro(1,1'-biphenyl)-4,4'-diyl) bis-1H-pyrrole-2,5-dione (140714-27-8), can be synthesized by the typical two-step process (Searle procedure) which is described in U.S. Pat. No. 6,503,421 B1. The two step process is found to give a typical yield of only 20%. Based on the reaction scheme and spectra analysis, the low yield of bismaleimide is likely attributed to the intermolecular imidization reaction of maleic amine acid which gives rise to a high molecular weight polymer instead of the desired intramolecular imidization reaction for bismaleimide. To improve the yield, a one-pot process (Vygotski method) was used in the present invention by refluxing the maleic anhydride and maleic diamine (in a 5 to 1 molar ratio) mixture in glacial acetic acid for 24 hours. The final product was purified by sublimation twice to obtain white crystalline bismaleimide.

2,3,5,6,-tetrachlorobenzene 1,4-dithiol (TCBDS) was synthesized by a rearrangement reaction from the corresponding diphenol. Bis(4-mercaptophenyl) sulfide (MPS), 2,2'-Dimercaptodiethyl sulfide (DMDS) and 4-Chloro-1,3-benzenedithiol (CBDS) were purchased and used as received without further purification.

Polymerization was performed as follows. Into a 100 ml glass flask equipped with a magnetic stirrer, a rubber septum and a nitrogen bulb were placed 1.972 g (4 mmol) OFBP-BMI, and 1.00 g (4 mmol) Bis(4-mercaptophenyl) sulfide monomer (MPS) and 50 grams of $C_7H_8O/C_6H_4(OH)CH_3$ (m-cresol) as the solvent. After injection into the glass flask of 25 mg of catalyst (triethylamine), the reaction was maintained at 40° C. for two hours. The resulting viscous polymer solution was slowly precipitated into an acidified solution of methanol/hydrochloric acid. The precipitated polymer was washed with warm methanol and then dried in a vacuum oven at 60° C. for 16 hours. The yield of white dry polymer powder was 2.52 grams (85%). Similar reactions can be carried out using TCBDS, DMDS and CBDS. Typical yields of the resulting polymer powder are in the range of about 70% to about 80%.

To test the influence of various reaction conditions on the Michael addition step-growth polymerization (Scheme 2), different reaction temperatures of about 20° C. and about 60° C. along with different solvents such as THF, cyclohexanone and DMF were used to prepare the polymer with the same set-up as above. Preferably, the solvent is selected from the group consisting of m-cresol, m-cresol derivatives, tetrahydrofuran (THF), cyclohexanone, and dimethylformamide (DMF). When the solvent is m-cresol, the reaction temperature may be maintained between about 20° C. and about 45° C. M-cresol provides lower temperatures in the polymerization process and side chain reactions are minimized, thus improved yields may be associated with the use of m-cresol.

Figure 2:
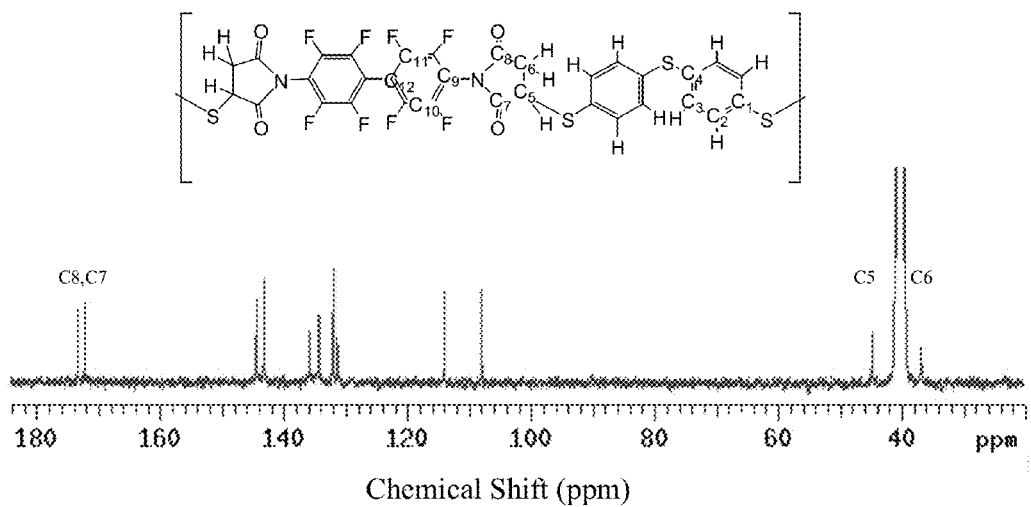
FIG. 2 is a $^{13}$C NMR spectrum of halogenated poly(imido sulfide) of the present invention according to Scheme 2.

A detailed spectral analysis (FTIR, $^1$H NMR, $^{13}$C NMR and $^{19}$F NMR) was performed and revealed the structure of an exemplary poly(imido sulfide) synthesized according to Scheme 2. The conclusive determination of the poly(imido sulfide) structure is shown in the FTIR results in FIG. 1 and in the $^{13}$C NMR spectrum of halogenated poly(imido sulfide) according to Scheme 2 as shown in FIG. 2 and DEPT $^{13}$C experiments.

Another embodiment of the present invention relates to electro-optic materials comprising a polymer having a poly(imido sulfide) backbone and an electro-optical chromophore having at least one terminal —SH group capable of reacting with a maleimide bond. The present invention provides covalently bonded mercaptofunctional chromophores and optical polymers. The electro-optical materials of the present invention can have a plurality of electro-optical chromophores each electro-optical chromophore having at least one terminal —SH group capable of reacting with a maleimide bond. Multiple —SH groups provide a branched polymer having multiple electro-optical chromophores.

Another embodiment of the present invention relates to electro-optical materials comprising a polymer having a poly(imido sulfide) backbone and an electro-optical chromophore having general Formula I:

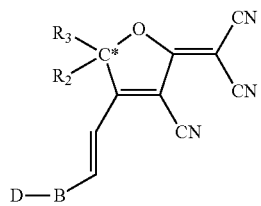

I wherein:
C* denotes a chiral carbon atom;
D is an electron donating group;
B comprises at least one bivalent ring;
$R_2$ and $R_3$ are different from one another; and
$R_2$ is selected from the group consisting of H, substituted or unsubstituted $C_1$-$C_{10}$ alkyl, substituted or unsubstituted $C_2$-$C_{10}$ alkenyl, substituted or unsubstituted $C_2$-$C_{10}$ alkynyl, substituted or unsubstituted aryl, substituted or unsubstituted alkylaryl, substituted or unsubstituted carbocycle, substituted or unsubstituted heterocycle, substituted or unsubstituted cyclohexyl, and $(CH_2)_n$—O—$CH_2)_n$ where n is an integer from 1 through 10; and $R_3$ is selected from the group consisting of substituted or unsubstituted aryl, substituted or unsubstituted alkylaryl, substituted or unsubstituted carbocycle, substituted or unsubstituted heterocycle, substituted or unsubstituted cyclohexyl, and $(CH_2)_n$—O—$(CH_2)_n$ where n is an integer from 1 through 10;

or $R_2$ and $R_3$ together form a ring structure or a substituted ring structure; and the compound of Formula I has, at any location, at least one terminal —SH group capable of reacting with a maleimide bond.

Preferably, the electro-optical chromophore is selected from the group consisting of the electro-optical chromophore having Formula II:

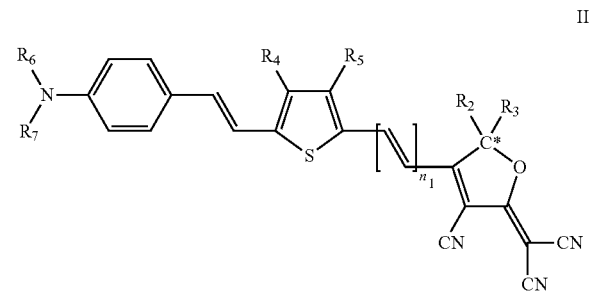

II wherein:
C* denotes a chiral carbon atom;
$R_2$ and $R_3$ are different from one another; and
$R_2$ is selected from the group consisting of H, substituted or unsubstituted $C_1$-$C_{10}$ alkyl, substituted or unsubstituted $C_2$-$C_{10}$ alkenyl, substituted or unsubstituted $C_2$-$C_{10}$ alkynyl, substituted or unsubstituted aryl, substituted or unsubstituted alkylaryl, substituted or unsubstituted carbocycle, substituted or unsubstituted heterocycle, substituted or unsubstituted cyclohexyl, and $(CH_2)_n$—O—$CH_2)_n$ where n is an integer from 1 through 10; and $R_3$ is selected from the group consisting of substituted or unsubstituted aryl, substituted or unsubstituted alkylaryl, substituted or unsubstituted carbocycle, substituted or unsubstituted heterocycle, substituted or unsubstituted cyclohexyl, and $(CH_2)_n$—O—$(CH_2)_n$ where n is an integer from 1 through 10; or $R_2$ and $R_3$ together form a ring structure or a substituted ring structure;

$R_4$ and $R_5$ can be the same or can be different and are selected from the group consisting of H, $C_nH_{2n+1}$, and SH; or $R_4$ and $R_5$ together or separately form an aromatic compound;

$R_6$ and $R_7$ can be the same or can be different and are selected from the group consisting of H, $CH_3$, SH and $(CH)_{n_2}$-Q, wherein Q is selected from the group consisting of H and SH and $n_2$ is an integer from 1 through 10; or $R_6$ and $R_7$ together or separately form an aromatic compound;

$n_1$ is an integer from 1 through 3; and the compound of Formula II has, at any location, at least one terminal —SH group capable of reacting with a maleimide bond;

and the electro-optical chromophore having Formula III:

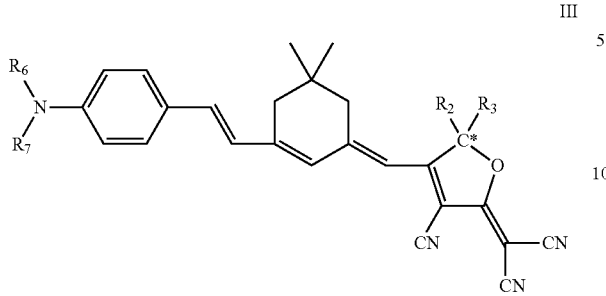

wherein:
- C* denotes a chiral carbon atom;
- $R_2$ and $R_3$ are different from one another; and
- $R_2$ is selected from the group consisting of H, substituted or unsubstituted $C_1$-$C_{10}$ alkyl, substituted or unsubstituted $C_2$-$C_{10}$ alkenyl, substituted or unsubstituted $C_2$-$C_{10}$ alkynyl, substituted or unsubstituted aryl, substituted or unsubstituted alkylaryl, substituted or unsubstituted carbocycle, substituted or unsubstituted heterocycle, substituted or unsubstituted cyclohexyl, and $(CH_2)_n$—O—$(CH_2)_n$ where n is an integer from 1 through 10; and
- $R_3$ is selected from the group consisting of substituted or unsubstituted aryl, substituted or unsubstituted alkylaryl, substituted or unsubstituted carbocycle, substituted or unsubstituted heterocycle, substituted or unsubstituted cyclohexyl, and $(CH_2)_n$—O—$(CH_2)_n$ where n is an integer from 1 through 10; or
- $R_2$ and $R_3$ together form a ring structure or a substituted ring structure;
- $R_6$ and $R_2$ can be the same or can be different and are selected from the group consisting of H, $CH_3$, SH and $(CH)_{n2}$-Q, wherein Q is selected from the group consisting of H and SH and $n_2$ is an integer from 1 through 10; or
- $R_6$ and $R_2$ together or separately form an aromatic compound; and
- the compound of Formula III has at any location, at least one terminal —SH group capable of reacting with a maleimide bond.

Preferably, at least one poly(imido sulfide) is halogenated. For example, the poly(imido sulfide) is selected from the group consisting of

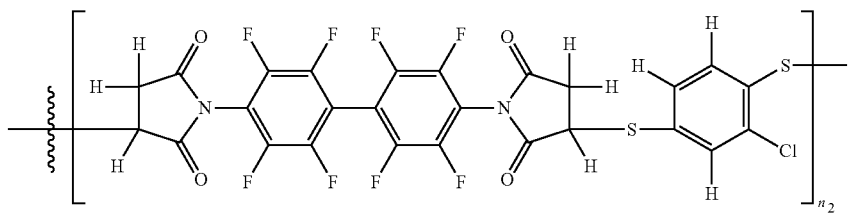

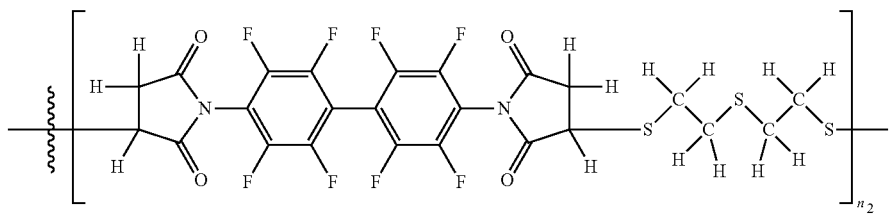

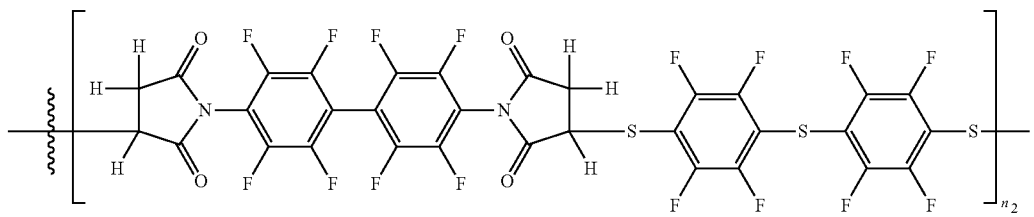

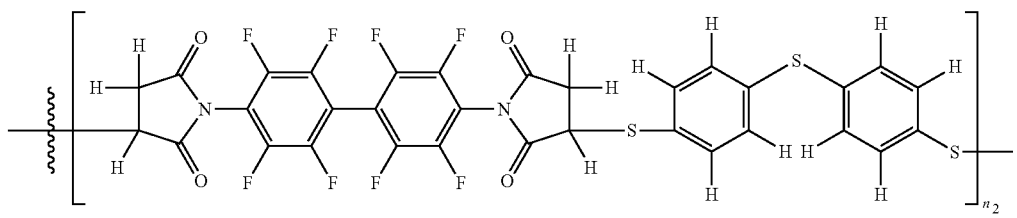

-continued

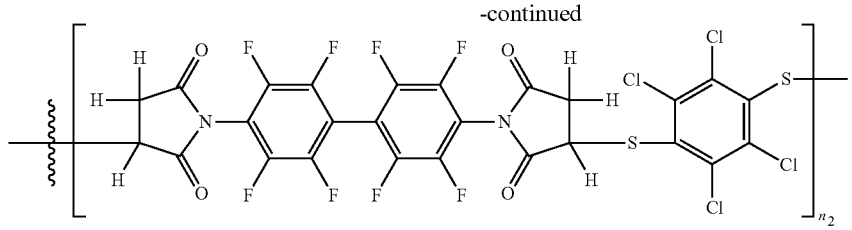

wherein:

$n_2$ is an integer greater than 20. Preferably, $n_2$ is an integer greater than 50.

Another embodiment of the present invention relates to a method of synthesizing an electro-optical material comprising a polymer having a halogenated poly(imido sulfide) backbone and an electro-optical chromophore having general Formula I:

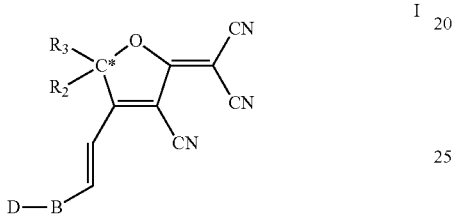

the method comprising reacting a sulfide with a N-(halogenated biphenyl) bismaleimide and with the optical chromophore in a solvent utilizing a triamine catalyst for example, triethylamine;

maintaining the reaction temperature between about 20° C. and about 60° C. for about two hours;

precipitating the resulting polymer into a solution of methanol and hydrochloric acid;

washing the resulting precipitated polymer with methanol;

drying the polymer in a vacuum oven in the range of about 60° C. to
  about 80° C. for about 16 hours thereby obtaining an EO material.

wherein, in the compound of Formula I;

C* denotes a chiral carbon atom;

D is an electron donating group;

B comprises at least one bivalent ring;

$R_2$ and $R_3$ are different from one another; and $R_2$ is selected from the group consisting of H, substituted or unsubstituted $C_1$-$C_{10}$ alkyl, substituted or unsubstituted $C_2$-$C_{10}$ alkenyl, substituted or unsubstituted $C_2$-$C_{10}$ alkynyl, substituted or unsubstituted aryl, substituted or unsubstituted alkylaryl, substituted or unsubstituted carbocycle, substituted or unsubstituted heterocycle, substituted or unsubstituted cyclohexyl, and $(CH_2)_n$—O—$(CH_2)_n$ where n is an integer from 1 through 10; and $R_3$ is selected from the group consisting of substituted or unsubstituted aryl, substituted or unsubstituted alkylaryl, substituted or unsubstituted carbocycle, substituted or unsubstituted heterocycle, substituted or unsubstituted cyclohexyl, and $(CH_2)_n$—O—$(CH_2)_n$ where n is an integer from 1 through 10;

or $R_2$ and $R_3$ together form a ring structure or a substituted ring structure; and the compound of Formula I has, at any location, at least one terminal —SH group capable of reacting with a maleimide bond.

Preferably, the solvent is selected from the group consisting of m-cresol, m-cresol derivatives, THF, cyclohexanone, and DMF. When the solvent is m-cresol, the reaction temperature may be maintained between about 20° C. and about 45° C. M-cresol provides lower temperatures in the polymerization process and side chain reactions are minimized, thus improved yields may be associated with the use of m-cresol.

Exemplary non-linear optical polymers can be synthesized by the following exemplary scheme:

Scheme 3

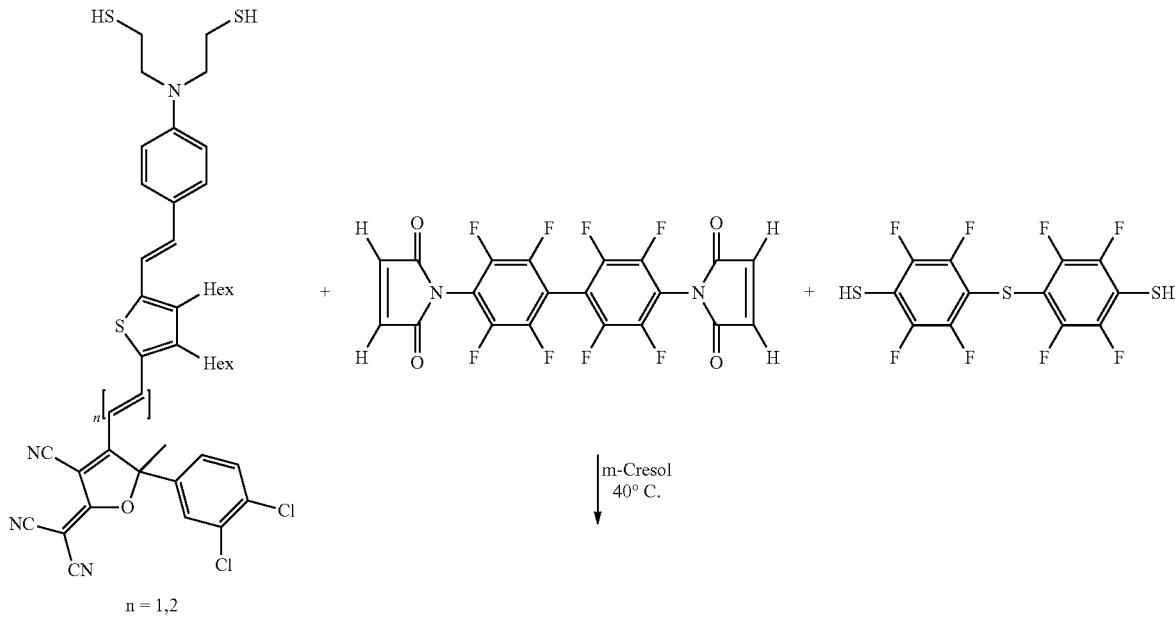

-continued

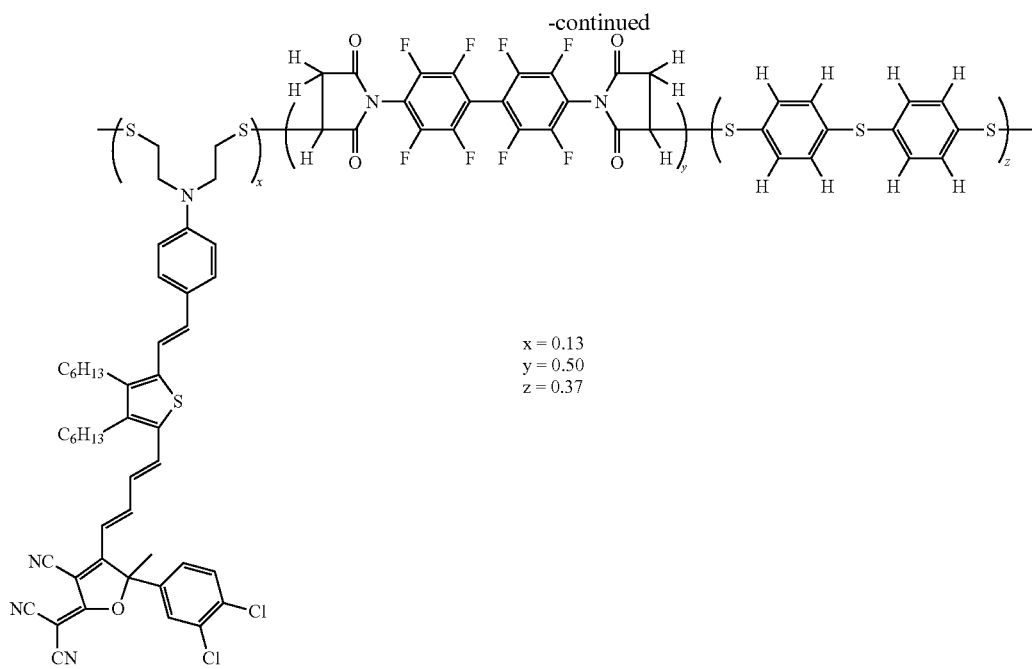

x = 0.13
y = 0.50
z = 0.37

The synthesis of linear electro-optical polymers was described above. The terpolymerization condition of nonlinear poly(imido sulfide) is the same as the linear Michael addition polymerization (Scheme 2). The covalent chemical bonded structure of terpolymer (Scheme 3) was confirmed by 1D NMR and 2D COSY NMR. The optical loss of terpolymer film on a silica substrate is 0.8 dB/cm measured from slab waveguide. From Differential Scanning calorimetry (DSC) measurement, the glass transition temperature of terpolymer is 157° C.

Bismaleimides can readily reacted with dithiols forming Michael type addition polymers. This is because those additions occur between electron deficient parts such as fluorinated aromatic compounds and electron rich parts such as thiols, under very mild polymerization conditions.

The EO chromophores of the present invention are covalently co-polymerized into a high Tg nonlinear EO polymer. High Tg polymers can keep the poled EO chromophores aligned in the EO polymer system at reasonably high temperatures. Covalently bonded EO polymers can also minimize phase separation leading to lower optical loss at communication wavelengths for example, 850 nm useful in indoor fiber networks, and 1300 nm-1550 nm.

For the reasons discussed above, the choice of proper functional groups on the EO chromophore for polymerization is important in assuring low optical loss in the synthesized EO nonlinear polymer. Mercaptofunctional high $\mu\beta$ chromophores are especially suited for use in electro-optical applications since they provide low optical loss at the aforementioned communication wavelengths. The EO chromophores of the present invention have at least one terminal —SH functional group located on the compound for reacting with a maleimide bond. Although these EO chromophores are sensitive to polymerization conditions, the method of synthesizing the EO materials of the present invention provides low temperature mild polymerization conditions which allow the sensitive mercaptofunctional high $\mu\beta$ EO chromophores to be incorporated into these EO materials. Also, since the EO materials obtained from this reaction provide very low optical loss due in part to the halogenated backbone, in particular the fluorinated backbone of the poly (imido sulfide) and very high glass transition temperature, mercaptofunctional high $\mu\beta$ EO chromophores are preferred in the preparation of non-linear EO polymers of the present invention.

The mercaptofunctional high $\mu\beta$ chromophores, halogenated poly(imido sulfide) linear optic polymers and nonlinear optic polymeric EO materials disclosed are suitable for electro-optical device applications such as systems and devices for emitting, modulating, transmitting or for sensing changes in light intensities.

The materials synthesized using Scheme 3 have a high Tg temperatures, low optical loss and result in solvent processable halogenated poly(imido sulfide) passive optical materials. These materials can be used to fabricate high Tg, low optical loss, low cost polymer waveguide components and thermally stable polymer host materials for electro-optical polymer modulators. Moreover, Michael addition reaction of halogenated bismaleimide with dithiol containing optical chromophores can be used to synthesize the covalent bonded high $\mu\beta$ EO polymers under mild polymerization conditions. These covalent bonded high $\mu\beta$ EO polymers exhibited a high Tg temperature (greater than about 150° C.) and low optical loss (~0.8 dB/cm) at major communication wavelengths for example, 1550 nm wavelengths.

It will be apparent to those skilled in the art that various modifications and variations can be made to the present invention without departing from the spirit or scope of the invention. Thus, it is intended that the present invention cover the modifications and variations of this invention provided they come within the scope of the appended claims and their equivalents.

The invention claimed is:
1. A method of synthesizing an electro-optical material comprising a polymer having a poly(imido sulfide) backbone and an electro-optical chromophore having general Formula I:

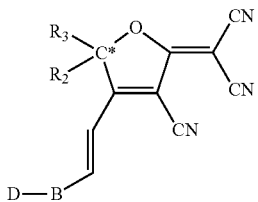

the method comprising
- reacting a sulfide with a N-(halogenated biphenyl) bismaleimide and with the optical chromophore in a solvent utilizing a catalyst;
- maintaining the reaction temperature between about 20° C. and about 60° C. for about two hours;
- precipitating the resulting polymer into a solution of methanol and hydrochloric acid;
- washing the resulting precipitated polymer with methanol;
- drying the polymer in a vacuum oven thereby obtaining an EO material;

wherein, in the compound of Formula I;
- C* denotes a chiral carbon atom;
- D is an electron donating group;
- B comprises at least one bivalent ring;
- $R_2$ and $R_3$ are different from one another; and
- $R_2$ is selected from the group consisting of H, substituted or unsubstituted $C_1$-$C_{10}$ alkyl, substituted or unsubstituted $C_2$-$C_{10}$ alkenyl, substituted or unsubstituted $C_2$-$C_{10}$ alkynyl, substituted or unsubstituted aryl, substituted or unsubstituted alkylaryl, substituted or unsubstituted carbocycle, substituted or unsubstituted heterocycle, substituted or unsubstituted cyclohexyl, and $(CH_2)_n$—O—$CH_2)_n$ where n is an integer from 1 through 10; and
- $R_3$ is selected from the group consisting of substituted or unsubstituted aryl, substituted or unsubstituted alkylaryl, substituted or unsubstituted carbocycle, substituted or unsubstituted heterocycle, substituted or unsubstituted cyclohexyl, and $(CH_2)_n$—O—$(CH_2)_n$ where n is an integer from 1 through 10;
- or $R_2$ and $R_3$ together form a ring structure or a substituted ring structure; and
- the compound of Formula I has, at any location, at least one terminal —SH group capable of reacting with a maleimide bond.

2. The method of claim 1 wherein the solvent is selected from the group consisting of m-cresol, m-cresol derivatives, tetrahydrofuran (THF), cyclohexanone, and dimethylformamide (DMF).

3. The method of claim 2 wherein the solvent is m-cresol and the reaction temperature is maintained between about 20° C. and about 45° C.

* * * * *